(12) United States Patent
Huang et al.

(10) Patent No.: US 12,100,501 B2
(45) Date of Patent: Sep. 24, 2024

(54) OBJECT ATTRIBUTE INFERENCE METHOD, STORAGE MEDIUM AND ELECTRONIC DEVICE

(71) Applicant: SHENZHEN UNIVERSITY, Shenzhen (CN)

(72) Inventors: Hui Huang, Shenzhen (CN); Qian Zheng, Shenzhen (CN); WeiKai Wu, Shenzhen (CN)

(73) Assignee: SHENZHEN UNIVERSITY, Shenzhen (CN)

( * ) Notice: Subject to any disclaimer, the term of this patent is extended or adjusted under 35 U.S.C. 154(b) by 627 days.

(21) Appl. No.: 17/266,256

(22) PCT Filed: Aug. 26, 2019

(86) PCT No.: PCT/CN2019/102641
§ 371 (c)(1),
(2) Date: Feb. 5, 2021

(87) PCT Pub. No.: WO2021/012348
PCT Pub. Date: Jan. 28, 2021

(65) Prior Publication Data
US 2021/0303833 A1    Sep. 30, 2021

(30) Foreign Application Priority Data
Jul. 23, 2019 (CN) .......................... 201910673879.9

(51) Int. Cl.
*G06K 9/00* (2022.01)
*G06F 18/21* (2023.01)
(Continued)

(52) U.S. Cl.
CPC ......... *G16H 30/40* (2018.01); *G06F 18/2148* (2023.01); *G06F 18/217* (2023.01);
(Continued)

(58) Field of Classification Search
CPC .... G16H 30/40; G16H 50/20; G06F 18/2148; G06F 18/217; G06F 18/214; G06F 18/24;
(Continued)

(56) References Cited

U.S. PATENT DOCUMENTS

2018/0232606 A1    8/2018  Park et al.

FOREIGN PATENT DOCUMENTS

| CN | 105389549 A   | 3/2016 |            |
|----|---------------|--------|------------|
| CN | 105872477 A * | 8/2016 | G06K 9/00342 |

(Continued)

OTHER PUBLICATIONS

International Search Report issued on Apr. 22, 2020 in corresponding International Application No. PCT/CN2019/102641; 7 pages.

*Primary Examiner* — Xin Jia
(74) *Attorney, Agent, or Firm* — Maier & Maier, PLLC (57) ABSTRACT

An object attribute inference method, a storage medium and an electronic device. The method includes the following steps: training a preset neural network by using a training sample comprising an action sequence and a target object attribute tag; where the action sequence is an interactive action sequence of a human body and an object. In this way, the object attribute inference model obtained through training can recognize the object attributes from the interaction action of the human body and the object, the object attributes include and are not limited to the weight, the shape, the hardness degree and the like of the object, and therefore the inference module obtained through training has the advantages of being universal in object attribute inference and wide in application range.

6 Claims, 4 Drawing Sheets

(51) Int. Cl.
  *G06F 18/214*  (2023.01)
  *G06N 3/08*  (2023.01)
  *G06N 5/04*  (2023.01)
  *G06V 10/44*  (2022.01)
  *G06V 10/62*  (2022.01)
  *G06V 20/64*  (2022.01)
  *G06V 40/20*  (2022.01)
  *G16H 30/40*  (2018.01)

(52) U.S. Cl.
  CPC ................. *G06N 3/08* (2013.01); *G06N 5/04* (2013.01); *G06V 10/454* (2022.01); *G06V 10/62* (2022.01); *G06V 20/64* (2022.01); *G06V 40/23* (2022.01)

(58) Field of Classification Search
  CPC ............ G06N 3/08; G06N 5/04; G06N 3/044; G06N 3/045; G06V 10/454; G06V 10/62; G06V 20/64; G06V 40/23; G06V 2201/033
  See application file for complete search history.

(56) References Cited

FOREIGN PATENT DOCUMENTS

| | | | | |
|---|---|---|---|---|
| CN | 108304790 A | | 7/2018 | |
| CN | 108388876 A | * | 8/2018 | ......... G06K 9/00268 |
| CN | 109409214 A | | 3/2019 | |
| CN | 109446927 A | | 3/2019 | |
| CN | 109492612 A | | 3/2019 | |
| CN | 109697395 A | * | 4/2019 | ......... G06K 9/00228 |

* cited by examiner

OBJECT ATTRIBUTE INFERENCE METHOD, STORAGE MEDIUM AND ELECTRONIC DEVICE

CROSS-REFERENCES TO RELATED APPLICATIONS

This application is a national stage application of PCT Patent Application No. PCT/CN2019/102641, filed on Aug. 26, 2019, which claims priority to Chinese Patent Application No. 201910673879.9, filed on Jul. 23, 2019, the content of all of which is incorporated herein by reference.

FIELD

The present disclosure relates to the technical field of computer graphics, and, more particularly, to an object attribute inference method, a storage medium and an electronic device thereof.

BACKGROUND

With a development of deep learning in recent years, a plurality of similar problems including human action behavior inference and more have been commonly solved by using neural network. At present, a plurality of existing inference methods generally use a recurrent neural network (RNN) structure to recognize a skeleton sequence or a convolutional neural network (CNN) to extract a characteristic of the skeleton sequence. A main difference between these methods is a representation of the skeleton sequence and the network structure. However, a plurality of existing inference methods are mainly aimed at a static posture of a human body with different behaviors, which limits a inference of a plurality of object attributes or properties from a human behavior.

SUMMARY

According to the above described defects, the purpose of the present disclosure is providing an object attribute inference method, a storage medium and an electronic device thereof.

A technical solution of the present disclosure to solve the technical problems is as follows:

An object attribute inference method, wherein comprising:
acquiring a training sample set, the training sample set comprises a plurality of groups of training samples, each group of training samples comprises an interactive action sequence of the training sample set, and a target object attribute tag;
inputting an action sequence in the training sample set into a preset neural network model, and obtaining a generated object attribute tag output from the preset neural network model;
correcting a plurality of model parameters of the preset neural network model, according to the target object attribute tag and the generated object attribute tag, until a training situation of the preset neural network model meets a plurality of preset conditions, to obtain an object attribute inference model having been trained.

The object attribute inference method, wherein the action sequence comprises a preset number of skeleton sequence frames, each skeleton sequence frame comprises a human skeleton data, wherein the human skeleton data is a tree-like sequence structure with joints as nodes.

The object attribute inference generation method, wherein the object attribute inference comprises a graph convolution module, a gated recurrent unit module, and a fully connected module; the step of inputting the action sequence in the training sample set into the preset neural network model, and obtaining the generated object attribute tag output from the preset neural network model, comprises:
inputting a joint feature of the action sequence into the graph convolution module, and extracting a joint feature applied for being input into the gated recurrent unit module through the graph convolution module, wherein an input of the graph convolution module comprises a joint position and a joint speed;
inputting the joint feature applied for being input into the gated recurrent unit module into the gated recurrent unit module, and outputting a joint feature at a time sequence dimension by the gated recurrent unit module, wherein the gated recurrent unit module has an attention sub-module arranged, the attention sub-module is applied to obtaining an weight coefficient of each joint to the object attribute;
inputting the weight coefficient and the joint features into the fully connected module, and outputting a generated object attribute tag corresponding to the action sequence through the fully connected module.

The object attribute inference generation method, wherein an expression of the joint feature output by the graph convolution module is:

$$x'_{t,i} = Relu\left(W_g\begin{bmatrix} x_{t,i} \\ x_{t,j} - x_{t,i} \end{bmatrix} + b\right),$$

wherein $x_{t,j}$ is a joint feature of an i-th joint input into the graph convolution module, j is an index of a parent node of i, t is a frame sequence number of human skeleton data frames, $W_g$ and b are two weight coefficients of the graph convolution module.

The object attribute inference generation method, wherein a calculation formula for the weight coefficient is:

$$a_{t,i} = \text{sigmoid}(W_{ha}H_{t-1} + W_{xa}\hat{x}_{t,i} + b_a),$$

wherein $W_{ha}$, $W_{xa}$, $b_a$ are three network parameters of a recurrent neural network, $\hat{x}_{t,i}$ is a joint feature of the i-th joint input into the gated recurrent unit module, $H_{t-1}$ is a hidden state of the recurrent neural network, t,t−1 are the frame sequence numbers of the human skeleton data frames.

An object attribute inference method based on an interactive action sequence, wherein the method applies any one of the object attribute inference models described above, comprising:
acquiring an interactive action sequence to be recognized, and inputting the interactive action sequence into the object attribute inference model having been trained;
recognizing the interactive action sequence through the object attribute inference model, to obtain an object attribute corresponding to the interactive action sequence.

The object attribute inference method based on the interactive action sequence, wherein the step of acquiring the interactive action sequence to be recognized, and inputting the interactive action sequence into the object attribute inference model having been trained, comprising:
acquiring an interactive action sequence to be recognized, and preprocessing the interactive action sequence, to obtain a preset number of image frames;

acquiring a human skeleton data frame corresponding to each image frame, and inputting all the human skeleton data frames obtained into the object attribute inference model having been trained, wherein the human skeleton data frames are arranged in an order of a frame time of the image frames.

A computer-readable storage medium, the computer-readable storage medium has one or more programs stored, and the one or more programs may be executed by one or more processors, to realize anyone of the steps in the object attribute inference method described above, or realize anyone of the steps in the object attribute inference method based on the interactive action sequence described above.

An electronic device, wherein comprising: a processor, a memory, and a communication bus; the memory has a computer-readable program that is able to be executed by the processor stored;

the communication bus realizes a connection and communication between the processor and the memory;

the processor executes the computer-readable program, to realize anyone of the steps in the object attribute inference method described above, or realize anyone of the steps in the object attribute inference method based on the interactive action sequence described above.

Benefits: comparing to the prior art, the present disclosure provides an object attribute inference method, a storage medium and an electronic device thereof, the method comprises: by training the preset neural network through the training samples comprising the action sequence and the target object attribute tag, the action sequence is an interaction action sequence between the human body and the object, so the object attribute inference model having been trained can recognize the object attribute from the interaction between the human body and the object. Wherein the object attributes may be a weight, a shape, a hardness and more of the object, which has expanded a comprehensiveness of the object attribute inference, thereby improving an adaptation scope of an object attribute inference model.

DETAILED DESCRIPTION OF THE EMBODIMENTS

The present disclosure provides an object attribute inference method, a storage medium and an electronic device thereof. In order to make the purpose, technical solution and the advantages of the present disclosure clearer and more explicit, further detailed descriptions of the present disclosure are stated here, referencing to the attached drawings and some embodiments of the present disclosure. It should be understood that the detailed embodiments of the disclosure described here are used to explain the present disclosure only, instead of limiting the present disclosure.

Those skilled in the art can understand that, unless specifically stated, the singular forms of "a", "an", "said" and "the" used herein may also include a plural form. It should be further understood that the term "comprising" used in the specification of the present disclosure refers to a presence of described features, integers, steps, operations, elements and/or components, without excluding a presence or addition of one or more other features, Integers, steps, operations, elements, components, and/or groups thereof. It should be understood that when we refer to an element as being "connected" or "coupled" to another element, it can be directly connected or coupled to the other element, or an intervening element may also be present. In addition, "connection" or "coupling" used herein may include wireless connection or wireless coupling. The term "and/or" as used herein includes all of one or more of all or a combination of any units and all associated listed items.

Those skilled in the art can understand that, unless otherwise defined, all terms (including technical terms and scientific terms) used herein have a same meaning as those commonly understood by those of ordinary skill in the art to which the present disclosure belongs. It should also be understood that terms such as those defined in a general dictionary should be understood to have a meaning consistent with the meaning in the context of the prior art, and unless being specifically defined as here, they will not be explained by an idealized or overly formal meaning.

Further explanations on the content of the present disclosure are stated hereafter, by a description to a plurality of embodiments in conjunction with a plurality of accompanying drawings.

Figure 1:
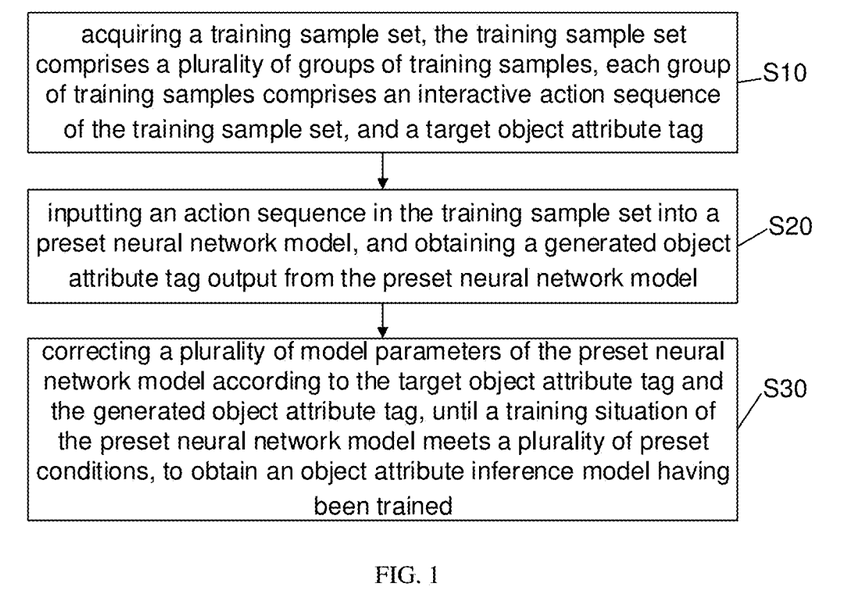
FIG. 1 illustrates a flow chart on the object attribute inference method provided by the present disclosure.

The present embodiment provides an object attribute inference method based on an interactive action sequence, shown as FIG. 1, the method comprises:

S10, acquiring a training sample set, the training sample set comprises a plurality of groups of training samples, each group of training samples comprises an interactive action sequence and a target object attribute tag;

The action sequence is an action sequence formed by human body interacting with object, and the target object attribute tag is an object attribute of the object interacting with the human body in the action sequence. In an embodiment, if the action sequence is an action sequence of a human body lifting a box with a weight of 5 kg, then the target object attribute tag is that the box weighs 5 kg.

Further, in an implementation of the present embodiment, the training samples may be classified according to a plurality of human body tags. For example, the human body tags corresponding to the training samples comprised in the training sample set, comprise: walking, fishing, dumping, bending an arm trainer, sitting down, drinking water, carrying boxes and carrying bowls; the training samples may be divided into walking training samples, fishing training samples, dumping training samples, arm trainer bending training samples, sitting training samples, water drinking training samples, box lifting training samples, and bowl moving training samples. Each of the object attribute is trained by adopting a corresponding training sample, for example, when training a box weight, the box lifting training samples are adopted for training; when training a water amount in a cup, the water drinking training samples are adopted for training.

Figure 2:
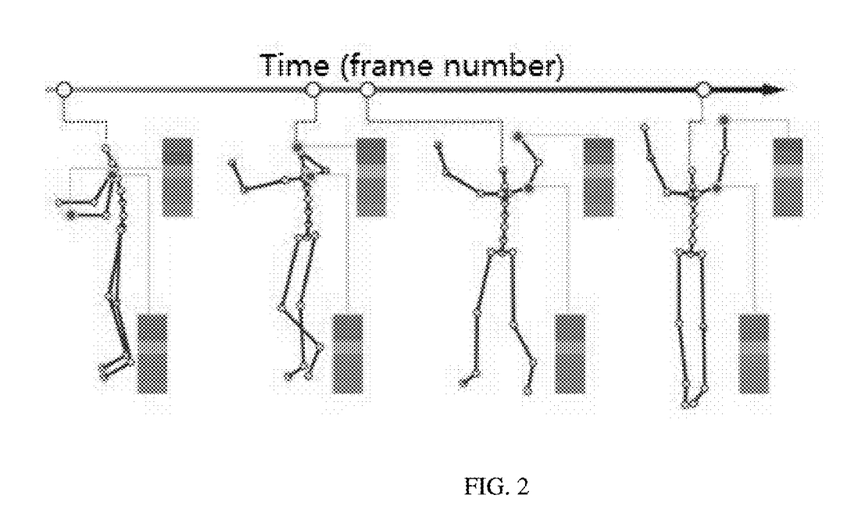
FIG. 2 illustrates a schematic diagram on the action sequence of the object attribute inference method provided by the present disclosure.

Further, in an implementation of the present embodiment, in order to facilitate learning the interactive action sequence, as shown in FIG. 2, the action sequence comprises a skeleton sequence formed by a preset number of skeleton sequence frames, wherein the skeleton sequence may be expressed as a three-dimensional frame of T×J×D, wherein T represents a frame sequence number of the sequence, J represents a number of a plurality of joint points on the skeleton, and D represents a dimension of the feature on each joint, wherein the number of the joint points is preferably 23. While each skeleton sequence frame comprises a human skeleton data, and the human skeleton data has a tree-like sequence structure with the joints as a plurality of nodes.

Figure 3:
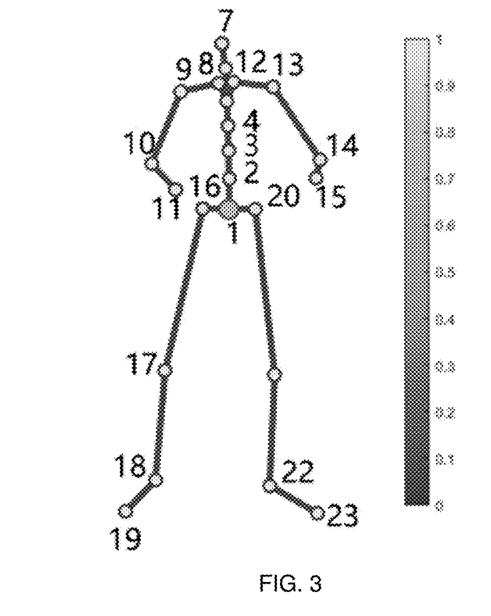
FIG. 3 illustrates a schematic diagram on a plurality of human skeleton joints of the object attribute inference method provided by the present disclosure.

Further, a plurality of positions of the human body joints are three-dimensional data, and the positions of the human body joints are defined in a local coordinate system in the human body. As shown in FIG. 3, an origin of the local coordinate system in the human body is on a pelvic joint (root node), with a Z axis perpendicular to a floor, and an X axis parallel to a forward direction of the pelvis, so that a global movement of the pelvis may be neglected, which reduces a complexity of a human bone data. In addition, in a human skeleton described in FIG. 3, a square in the skeleton sequence represents a joint feature of the joints on each frame. Wherein, the joint feature comprises a joint position and a joint speed, and the joint speed refers to a difference between a joint position of a joint point in a next previous skeleton sequence frame and a joint position of a same joint point in a current skeleton sequence frame. In an embodiment, an i-th joint in the t-th frame is recorded as $J_i^t$, then the joint speed $S_i^t$, is approximately a difference between two coordinates of the joints in a time dimension $S_i^t = J_i^{t+1} - J_i^t$.

At the same time, in the present embodiment, the preset number of skeleton sequence frames is obtained by processing a human-object interactive action animation acquired, and the human-object interactive action animation may be acquired through an action capture device. In an embodiment, the human body may wear an MVN inertial action capture suit, to capture a plurality of human action through the MVN inertial action capture suit, before saving in a form of a three-dimensional skeleton sequence; the human body may wear a sports camera on his head and record a plurality of first-view video thereof. In addition, around the human body, there are three cameras arranged to record three videos in different perspectives through the three cameras, that may make the training samples comprise the three-dimensional skeleton action sequence, a RGB video corresponding to the three-dimensional skeleton action sequence, and the object attributes of an interactive object, wherein the object attributes may comprise but not limited to weight, length, volume, hardness, and more.

In addition, since a duration of the action sequence collected is different to each other, in order to improve a training speed of the preset neural network, after obtaining the action sequence, it is possible to process the action sequence, and select a preset number of image frames from the action sequence, and obtain a human skeleton data frame corresponding to each of the image frames, and take all the human skeleton data frames acquired as the action sequence, wherein a number of the human skeleton data frames is preferably 30 frames. In addition, in order to increase a number of the training samples, after obtaining the action sequence, rotate each action sequence around a direction of gravity 10 times, before cutting into 10 sub-sequences as an action sequence being enhanced. Wherein a rotation angle obeys a uniform distribution, between [0,π]. A length of a cropped subsequence is [0.9,1] of an original sequence, and following a uniform distribution.

S20, inputting an action sequence in the training sample set into a preset neural network model, and obtaining a generated object attribute tag output from the preset neural network model.

Figure 4:
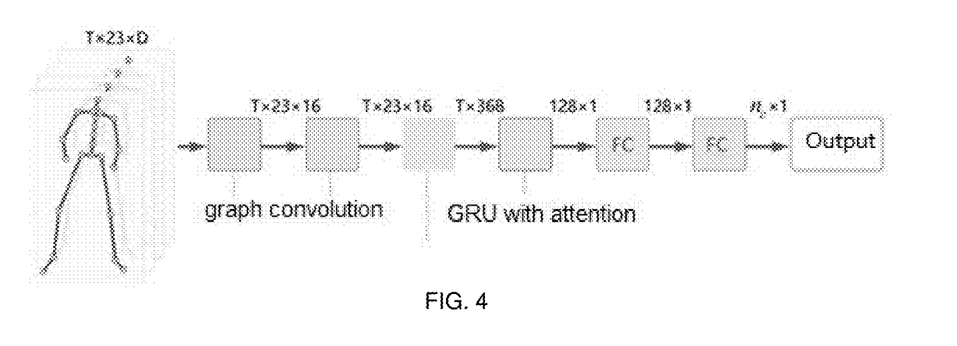
FIG. 4 illustrates a flowchart on a processing procedure of the preset neural network in the object attribute inference method, provided by the present disclosure.
Figure 5:
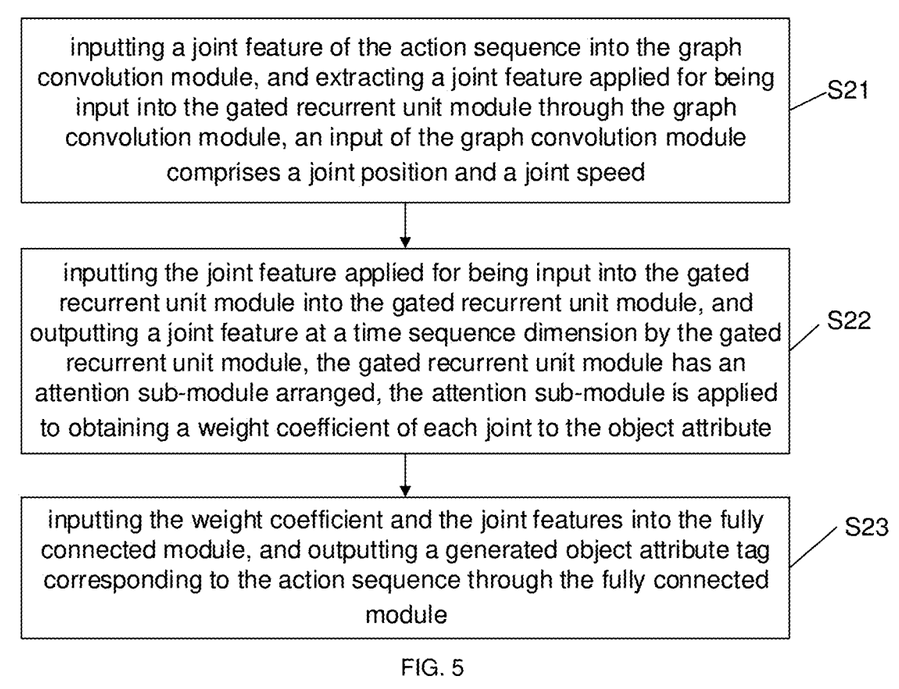
FIG. 5 illustrates a schematic flowchart on step S20 in the object attribute inference method provided by the present disclosure.

The preset neural network comprises a graph convolution module, a gated recurrent unit module, and a fully connected module. The graph convolution module is used to calculate a feature of each joint according to a known human skeleton topology. The gated recurrent unit module is a gated recurrent unit module with an attention mechanism. The attention mechanism is applied to fusing all frames' information and giving an importance of each m-joints to a target object attribute tag. Correspondingly, as shown in FIG. 4 and FIG. 5, the step of inputting an action sequence in the training sample set into a preset neural network model, and obtaining a generated object attribute tag output from the preset neural network model, comprises:

S21, inputting a joint feature of the action sequence into the graph convolution module, and extracting a joint feature applied for being input into the gated recurrent unit module through the graph convolution module, wherein an input of the graph convolution module comprises a joint position and a joint speed.

Inputting the joint feature applied for being input into the gated recurrent unit module into the gated recurrent unit module, and outputting a joint feature at a time sequence dimension by the gated recurrent unit module, wherein the gated recurrent unit module has an attention sub-module arranged, the attention sub-module is applied to obtaining a weight coefficient of each joint to the object attribute.

S22, inputting the joint feature applied for being input into the gated recurrent unit module into the gated recurrent unit module, and outputting a joint feature at a time sequence dimension by the gated recurrent unit module, wherein the gated recurrent unit module has an attention sub-module arranged, the attention sub-module is applied to obtaining a weight coefficient of each joint to the object attribute.

S23, inputting the weight coefficient and the joint features into the fully connected module, and outputting a generated object attribute tag corresponding to the action sequence through the fully connected module.

Since the human skeleton data is a tree-like structure, when performing a graph convolution operation, for each joint, take a parent node of the joint only as an adjacent node of the joint, then for an i-th joint in a t-th human skeleton data frame, after being treated by the graph convolutional module, a joint feature of is as follows:

$$x'_{t,i} = Relu\left(W_g \begin{bmatrix} x_{t,i} \\ x_{t,j} - x_{t,i} \end{bmatrix} + b\right),$$

wherein $x_{t,i}$ is a joint feature of an i-th joint input into the graph convolution module, j is an index of a parent node of i, t is a frame sequence number of human skeleton data frames, $W_g$ and b are two weight coefficients of the graph convolution module.

Figure 6:
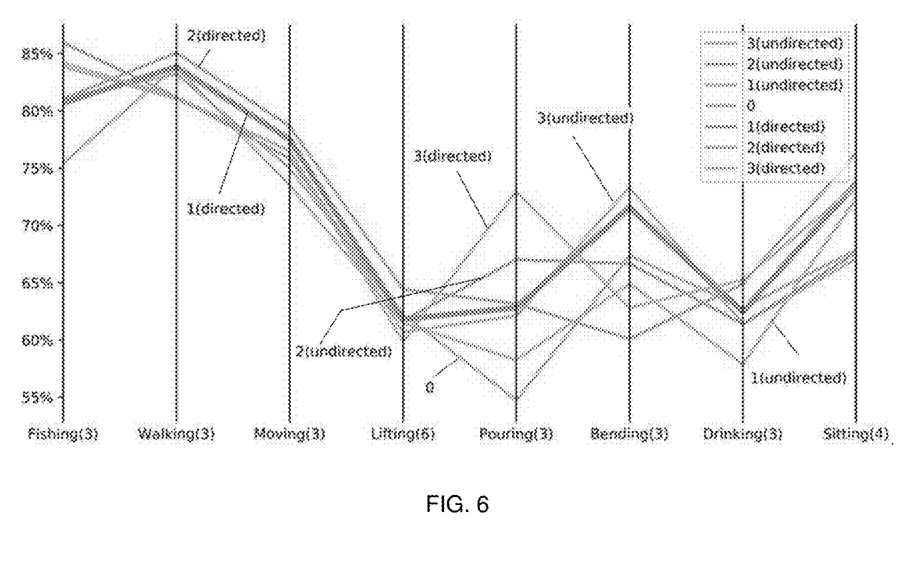
FIG. 6 illustrates a chart on the accuracy of different graph convolution methods under different attribute inference tasks in the object attribute inference method provided by the present disclosure.

In addition, in order to illustrate that the human skeleton is treated as a tree-like structure, the parent node of the joint is used as a neighborhood, and by adopting the graph convolution module to calculate the joint features, it is possible to improve the accuracy of the object attribute inference model for an attribute inference. Assuming that all other layers in a network are fixed, while settings of the two graph convolutional modules are changed, an impact of different graph convolutional modules on an inference accuracy of the object attribute is recorded. The settings of the two graph convolutional modules are respectively: 1. neglecting a bone connection relationship between the joint points, and only considering the joint itself to calculate the joint features; 2. regarding the human skeleton as a tree-like structure, which is a directed graph; 3. regarding the human skeleton as an undirected graph. At the same time, an impact of taking different numbers of neighboring points on the result was tested. In the test, k=1, 2, 3. A test result is shown in FIG. 6. Each line in the figure represents an attribute inference accuracy rate of different graph convolution settings in different tasks. It can be seen from FIG. 6 that treating the human skeleton as a tree-like structure and only considering the parent node of the joint as the neighborhood, can make the object attribute inference model have good accuracy.

Further, the gated recurrent unit module with the attention mechanism is adding a gate for judging an importance of a joint into the recurrent neural network. The importance of each joint can be calculated by a hidden state $H_{t-1}$ of the recurrent neural network, so that a joint and a human skeleton data frame that contribute a lot to recognize the object attributes will be found, that is, a key joint and a key human skeleton data frame will be obtained. In the present implementation, a calculation formula for the weight coefficient is:

wherein $W_{ha}$, $W_{xa}$, $b_a$ are three network parameters of a recurrent neural network, $\hat{x}_{t,i}$ is a joint feature of the i-th joint input into the gated recurrent unit module, $H_{t-1}$ is a hidden state of the recurrent neural network, t,t−1 are the frame sequence numbers of the human skeleton data frames.

S30, correcting a plurality of model parameters of the preset neural network model, according to the target object attribute tag and the generated object attribute tag, until a training situation of the preset neural network model meets a plurality of preset conditions, to obtain an object attribute inference model having been trained.

The preset condition comprises that a loss value meets a preset requirement or a number of training times reaches a preset number of times. The preset requirement may be determined according to an accuracy of the human body action editing model, which will not be described in details here. The preset number of times may be a maximum number of training times of the preset neural network, for example, 1000 times or else. Therefore, outputting the generated action sequence from the preset neural network, and calculating the loss value of the preset neural network according to the generated action sequence and the target action sequence. After calculating and obtaining the loss value, the loss value is judged to decide if it has met a preset requirement: if the loss value has met the preset requirement, the training will be finished; if the loss value has not met the preset requirement, then whether the training times of the preset neural network has reached the preset number of times is judged, and if the preset number of times is not reached, then the network parameters of the preset neural network are corrected according to the loss value; if the preset number of times is reached, the training ends. Thus judging whether training the preset neural network shall be completed or not by the loss value and the number of training times, may avoid training the preset neural network from reaching an infinite loop due to the loss value impossible to meet the preset requirement.

In addition, in a process of providing the object attribute inference method, the present embodiment provides a training sample data set. The training sample data set comprises 100 subjects, and each subject made 8 groups of interactive actions with a plurality of different objects, wherein the subjects are 20-35 years old, 150 cm-195 cm tall, male and female, and different in strength.

1. Data Collection Method

The training sample data set adopts a multi-input source data to construct a data set. When the subject performs an action, an MVN inertial motion capture suit will be worn, to capture a plurality of human actions before saving in a form of a three-dimensional skeleton sequence; the subject will wear a sports camera on head, to record the subject's first-view video. In addition, three cameras fixed around the subjects are also applied to recording videos with three different perspectives. Of course, in a practical application, it is also possible to obtain a three-dimensional skeleton data by other methods that can collect the three-dimensional skeleton data.

2. Human-Object Interactive Action

The subject will interact with multiple objects of a same kind but different attributes, wherein the interactive action comprises walking, fishing, pouring, arm machine bending, sitting, water drinking, box lifting and bowl moving.

The interactive action of walking is applied to inferring a width of a road from a walking action, that is, an object attribute corresponding to the interactive action of walking is a road width. A collection process of the interactive action of walking is: each subject reciprocates once on three roads with different widths. Two straight lines are stuck on a floor to represent a road, when the subject is walking on the road, a motion range of his feet should always be between the straight lines, without touching the straight lines at an edge.

The interactive action of fishing is applied to inferring a length of a fishing rod, that is, an object attribute corresponding to the interactive action of fishing is the length of the fishing rod. A collection process of interactive action of fishing is as follows: each subject adopts three fishing rods in different lengths with magnet on an end, to "fish" a magnet fish on the floor.

The interactive action of dumping is applied to inferring a type of a content contained in a cup, that is, an object attribute corresponding to the interactive action of dumping is a type of content in the cup. A collection process of the interactive action of dumping is: each subject will dump the contents in three cups into three other cups, wherein, the contents in the three cups are water, laundry detergent and rice respectively.

The interactive action of bending the arm machine is applied to inferring a force required for bending the arm machine, that is, the object attribute corresponding to the interactive action of bending the arm machine is power. A collection process of the interactive action of bending the arm machine is: the subject will bend three arm machines with different strength, wherein three strengths of the arm machine are from weak to strong.

The interactive action of sitting is applied to inferring a hardness of a stool, that is, an object attribute corresponding to the interactive action of sitting is the hardness of the stool. A collection process of the interactive action of sitting is: the subject sits down onto four stools of a same height but different hardness, for example, a hardest stool is a plastic stool, and a softest stool is an under-inflated yoga ball.

The interactive action of drinking water is applied to inferring an amount of water in a cup, that is, an object attribute corresponding to the interactive action of drinking water is a volume of the water in the cup. A collection process of the interactive action of drinking water is: three cups with different amount of water are placed on a table, the subject will pick up a cup in turn and take a sip, before putting down. Wherein a volume of the water in the three cups may be equal to a volume of the cup, half the volume of the cup, and zero.

The interactive action of box lifting is applied to inferring a weight of the box from an action of a subject lifting a box, that is, an object attribute corresponding to the interactive action of box lifting is a weight of the box. A collection process of the interactive action of box lifting is: the subject will continue lifting a box to four different heights: 1. Lifting the box from the floor to a sofa. 2. Lifting the box from the sofa to a table. 3. Lifting the box from the table to a top of a bookcase. 4. Placing the box back onto the floor. Before lifting the box, the subject will not know a weight of the box, and the box may have 6 different weights, unequally from 0 to 25 kilograms, while each different box has a difference of 5 kg, and the subject will move sequentially the boxes having been disordered.

The interactive action of bowl moving is applied to inferring a degree to which a content in the bowl is easily spilled, that is, an object attribute corresponding to the interactive action of bowl moving is the extent to which the content in the bowl is spilled, and a collection process of the interactive action of bowl moving is: the subjects will successively move three bowls to four different heights in a sequence, wherein, all the three bowls are not equipped with bowl cover, while two bowls are filled with rice and water respectively, and one bowl is empty.

3. Evaluating an Object Attribute Inference Result

Dividing the data into three parts: a training set, a validation set, and a test set, to test a performance of the model in inferring the object attributes. Dividing 100 skeletal sequence of the subjects interacting with the object into the three parts described above, the training set has 60 subjects, each of the validation set and the test set contains 20 subjects, and a sequence of a same subject is guaranteed not appear in three subsets described above at a same time. In a process of network training, taking a network parameter with a smallest verification error as the network parameter of the object attribute inference model, and inputting a plurality of test data contained in the test set sequentially to the object attribute inference model.

Inputting sequentially the test set corresponding to each interactive action into the object attribute inference model, and a inference accuracy of the object attribute inference model for the object attribute corresponding to each interactive action is shown in table 1. For example, for an action sequence set of box lifting, wherein the weights of the boxes in the action sequence set of box lifting are 0 kg, 5 kg, 10 kg, 15 kg, 20 kg and 25 kg, respectively. A inference result from the object attribute inference model is shown in table 1, and the accuracy of the object attribute inference model is about 62%.

TABLE 1

The accuracy of object attribute inference under different tasks

| Object attribute | accuracy |
|---|---|
| Lifting box to infer weight(6) | 61.8 |
| Moving bowls to infer degree of spill (3) | 77.5 |
| Walking to infer width of road (3) | 83.9 |
| Fishing to infer fishing rod length (3) | 80.7 |
| Dumping to infer liquid type(3) | 62.8 |
| Bending to infer arm machine strength (3) | 71.6 |
| Sitting down to infer hardness of stool(4) | 73.7 |
| Drinking water to infer water amount in cup (3) | 62.5 | wherein the number in the parenthesis behind each object attribute indicates a number of the object attributes, for example, a six in the "lifting boxes to infer weight(6)" indicates that a number of different box weights is six.

4. Evaluating an Impact of a Data Representation Form of Different Skeleton Sequences on the Accuracy of the Attribute Inference The data representation form refers to a dynamic attribute of human action during a same period of human action, wherein the dynamic attribute may be represented by a position coordinate of the joint, a rotation matrix of the bone, a movement speed of the joint, a rotational angular velocity between different bones and more. The attribute inference of three kinds of objects is tested herein, wherein the interactive actions are box lifting, walking and fishing, the impact of a plurality of data representation forms and a plurality of combinations thereof is evaluated herein. Each data representation form is shown in table 2. Table 2 shows a performance of the attribute inference in different representation forms. It can be seen that by using the joint position plus the joint speed, it has a best overall performance. So a same setting will be applied in a plurality of subsequent tests.

TABLE 2 shows an accuracy of the attribute inference in different representation forms.

| | Lifting Box (6) | Walking (3) | Fishing (3) |
|---|---|---|---|
| Position | 57.82 | 76.84 | 84.21 |
| Euler angle | 43.38 | 81.58 | 73.68 |
| Velocity | 59.93 | 79.82 | 69.40 |
| Angular velocity | 47.46 | 73.16 | 63.51 |
| Position& Euler angle | 55.70 | 79.65 | 71.58 |
| Position& velocity | 61.81 | 83.93 | 80.70 |
| Position& angular velocity | 64.58 | 79.47 | 77.54 |
| Velocity& angular velocity | 55.70 | 84.39 | 76.49 |
| Velocity& Euler angle | 50.56 | 70.00 | 66.67 |
| Euler angle& angular velocity | 56.06 | 80.53 | 72.28 |
| Position, Euler angle& angular velocity | 50.35 | 78.42 | 70.18 |
| Position, velocity& angular velocity | 62.32 | 82.98 | 78.95 |
| Position, Euler angle& velocity | 56.55 | 81.58 | 71.93 |
| Position, Euler angle, velocity & angular velocity | 58.73 | 82.98 | 78.95 |

Based on the object attribute inference method, the present disclosure further provides an object attribute inference method based on the interactive action sequence, wherein the method applies any one of the object attribute inference models described above, comprising:

acquiring an interactive action sequence to be recognized, and inputting the interactive action sequence into the object attribute inference model having been trained;

recognizing the interactive action sequence through the object attribute inference model, to obtain an object attribute corresponding to the interactive action sequence.

The object attribute inference method based on the interactive action sequence, wherein the step of acquiring the interactive action sequence to be recognized, and inputting the interactive action sequence into the object attribute inference model having been trained, comprising:

acquiring an interactive action sequence to be recognized, and preprocessing the interactive action sequence, to obtain a preset number of image frames;

acquiring a human skeleton data frame corresponding to each image frame, and inputting all the human skeleton data frames obtained into the object attribute inference model having been trained, wherein the human skeleton data frames are arranged in an order of a frame time of the image frames.

According to the object attribute inference method based on the interactive action sequence and the object attribute inference method, the present disclosure further provides a computer-readable storage medium, the computer-readable storage medium has one or more programs stored, and the one or more programs may be executed by one or more processors, to realize anyone of the steps in the object attribute inference method described above, or realize anyone of the steps in the object attribute inference method based on the interactive action sequence described above.

Figure 7:
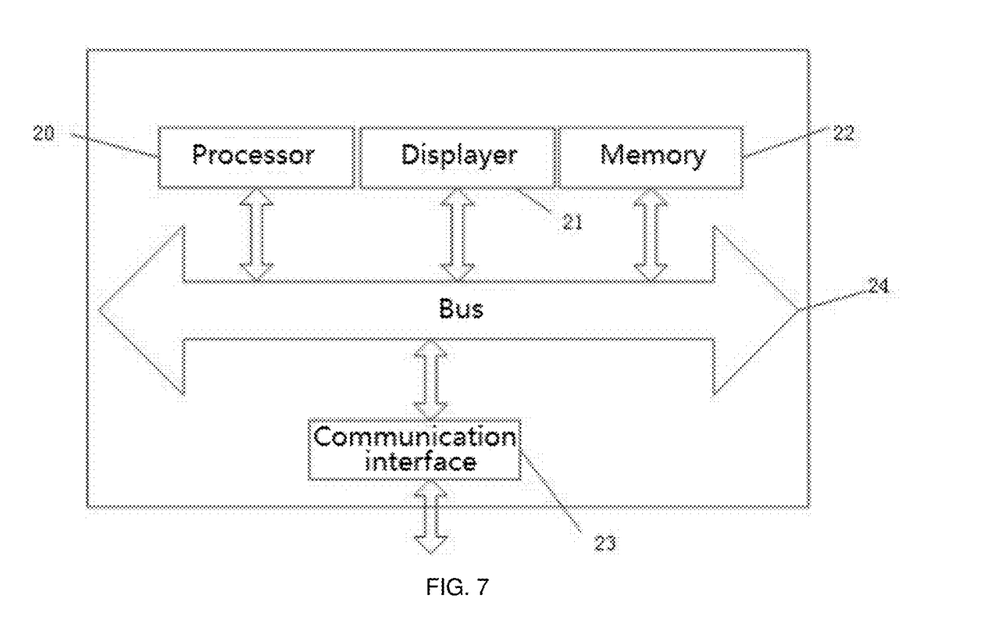
FIG. 7 illustrates a schematic structural diagram on an electronic device provided by the present disclosure.

According to the object attribute inference method based on the interactive action sequence and the object attribute inference method, the present disclosure further provides an electronic device, shown as FIG. 7, comprising at least one processor 20, a displayer 21, and a memory 22, and may further comprising a communication interface 23 and a bus 24. The processor 20, the displayer 21, the memory 22 and the communication interface 23 may achieve a communication between each other through the bus 24. The displayer 21 is arranged to display a user guide interface preset in an initial setting mode. The communication interface 23 may transmit information. The processor 20 may call a plurality of logic instructions in the memory 22, to execute the method in the embodiments described above.

In addition, the logic instructions in the memory 22 described above may be implemented in a form of a plurality of software functional units and when being sold or used as an independent product, the logic instructions may be stored in a computer-readable storage medium.

As a computer-readable storage medium, the memory 22 may be configured to store a plurality of software programs and computer-executable programs, including a plurality of program instructions or modules corresponding to the methods in the embodiments of the present disclosure. The processor 20 executes a plurality of functional applications and data processes by running the software programs, instructions or modules stored in the memory 22, that is, implements the methods stated in the embodiments described above.

The memory 22 may comprise a program storage area and a data storage area. The program storage area may store an operating system and an application program required by at least one function; the data storage area may store data created according to a use of the terminal device. In addition, the memory 22 may include a high-speed random access memory, and may also include a non-volatile memory. For example, U disk, mobile hard disk, read-only memory (ROM), random access memory (RAM), magnetic disk or optical disk and other media that can store program codes, or temporary State storage medium.

In addition, the specific process of the storage media and the processors loading and executing the multiple instructions in the electronic device has been described in details in the method described above, and will not be described herein again.

It should be understood that, the application of the present disclosure is not limited to the above examples listed. Ordinary technical personnel in this field can improve or change the applications according to the above descriptions, all of these improvements and transforms should belong to the scope of protection in the appended claims of the present disclosure.

What is claimed is:

1. An object attribute inference method, comprising:

acquiring a training sample set, wherein the training sample set comprises a plurality of groups of training samples, and each group of training samples comprises both an interactive action sequence of the training sample set and a target object attribute tag;

inputting an action sequence in the training sample set into a preset neural network model, wherein the action sequence comprises a preset number of skeleton sequence frames, each skeleton sequence frame comprises human skeleton data comprising a tree-like sequence structure with joints as nodes;

obtaining a generated object attribute tag output from the preset neural network model; and correcting a plurality of model parameters of the preset neural network model according to the target object attribute tag and the generated object attribute tag, until a training situation of the preset neural network model meets a plurality of preset conditions, to obtain an object attribute inference model, wherein the object attribute inference model comprises a graph convolution module, a gated recurrent unit module, and a fully connected module;

inputting a joint feature of the action sequence into the graph convolution module;

extracting a joint feature applied for being input into the gated recurrent unit module through the graph convolution module, an input of the graph convolution module comprising a joint position and a joint speed;

inputting the joint feature applied for being input into the gated recurrent unit module into the gated recurrent unit module;

outputting a joint feature at a time sequence dimension by the gated recurrent unit module, the gated recurrent unit module has an attention sub-module arranged, and the attention sub-module is applied to obtaining a weight coefficient of each joint to the object attribute;

inputting the weight coefficient and the joint features into the fully connected module; and outputting a generated object attribute tag corresponding to the action sequence through the fully connected module.

2. The object attribute inference method according to claim 1, wherein an expression of the joint feature output by the graph convolution module is:

$$x'_{t,i} = Relu\left(W_g \begin{bmatrix} x_{t,i} \\ x_{t,j} - x_{t,i} \end{bmatrix} + b\right).$$

$x_{t,i}$ is a joint feature of an i-th joint input into the graph convolution module, j is an index of a parent node of i, t is a frame sequence number of human skeleton data frames, and $W_g$ and b are two weight coefficients of the graph convolution module.

3. The object attribute inference method according to claim 1, wherein a calculation formula for the weight coefficient is:

$$a_{t,i} = \text{sigmoid}(W_{ha}H_{t-1} + W_{xa}\hat{x}_{t,i} + b_a),$$

$W_{ha}$, $W_{xa}$, $b_a$ are three network parameters of a recurrent neural network, $\hat{x}_{t,i}$ is a joint feature of the i-th joint input into the gated recurrent unit module, and $H_{t-1}$ is a hidden state of the recurrent neural network, t,t−1 are the frame sequence numbers of the human skeleton data frames.

4. The object attribute inference method according to claim 1, further comprising:
acquiring an interactive action sequence to be recognized;
inputting the interactive action sequence into the object attribute inference model having been trained; and
recognizing the interactive action sequence through the object attribute inference model, to obtain an object attribute corresponding to the interactive action sequence.

5. The object attribute inference method according to claim 4, wherein acquiring the interactive action sequence to be recognized, and inputting the interactive action sequence into the object attribute inference model having been trained, further comprises:
acquiring an interactive action sequence to be recognized;
preprocessing the interactive action sequence, to obtain a preset number of image frames;
acquiring a human skeleton data frame corresponding to each image frame; and
inputting all the human skeleton data frames obtained into the object attribute inference model having been trained, and the human skeleton data frames are arranged in an order of frame time of the image frames.

6. An electronic device, comprising:
a processor,
a memory, and
a communication bus; the memory storing a computer-readable program that is executed by the processor;
the communication bus realizes a connection and communication between the processor and the memory; and
the processor executes the computer-readable program to realize the steps in an object attribute inference method comprising:
acquiring a training sample set, the training sample set comprises a plurality of groups of training samples, each group of training samples comprises an interactive action sequence of the training sample set, and a target object attribute tag;
inputting an action sequence in the training sample set into a preset neural network model, wherein the action sequence comprises a preset number of skeleton sequence frames, each skeleton sequence frame comprises human skeleton data comprising a tree-like sequence structure with joints as nodes;
obtaining a generated object attribute tag output from the preset neural network model;
correcting a plurality of model parameters of the preset neural network model according to the target object attribute tag and the generated object attribute tag, until a training situation of the preset neural network model meets a plurality of preset conditions, to obtain an object attribute inference model, wherein the object attribute inference model comprises a graph convolution module, a gated recurrent unit module, and a fully connected module;
inputting a joint feature of the action sequence into the graph convolution module;
extracting a joint feature applied for being input into the gated recurrent unit module through the graph convolution module, an input of the graph convolution module comprising a joint position and a joint speed;
inputting the joint feature applied for being input into the gated recurrent unit module into the gated recurrent unit module;
outputting a joint feature at a time sequence dimension by the gated recurrent unit module, the gated recurrent unit module has an attention sub-module arranged, and the attention sub-module is applied to obtaining a weight coefficient of each joint to the object attribute;
inputting the weight coefficient and the joint features into the fully connected module; and
outputting a generated object attribute tag corresponding to the action sequence through the fully connected module.

\* \* \* \* \*